(12) United States Patent
Mattke et al.

(10) Patent No.: US 8,779,181 B2
(45) Date of Patent: Jul. 15, 2014

(54) PROCESS FOR PREPARING ISOCYANATES

(75) Inventors: Torsten Mattke, Freinsheim (DE); Carsten Knoesche, Niederkirchen (DE)

(73) Assignee: BASF SE, Ludwigshafen (DE)

( * ) Notice: Subject to any disclaimer, the term of this patent is extended or adjusted under 35 U.S.C. 154(b) by 404 days.

(21) Appl. No.: 13/123,787

(22) PCT Filed: Oct. 8, 2009

(86) PCT No.: PCT/EP2009/063071
§ 371 (c)(1),
(2), (4) Date: Apr. 12, 2011

(87) PCT Pub. No.: WO2010/043532
PCT Pub. Date: Apr. 22, 2010

(65) Prior Publication Data
US 2012/0016154 A1      Jan. 19, 2012

(30) Foreign Application Priority Data

Oct. 15, 2008   (EP) .................................. 08166624

(51) Int. Cl.
*C07C 263/10*   (2006.01)
*C07C 265/14*   (2006.01)

(52) U.S. Cl.
USPC ........................................................ 560/347

(58) Field of Classification Search
CPC ............................ C07C 263/10; C07C 265/12
See application file for complete search history.

(56) References Cited

U.S. PATENT DOCUMENTS

| | | | |
|---|---|---|---|
| 7,488,842 B2 * | 2/2009 | Knoesche | 560/347 |
| 7,541,487 B2 | 6/2009 | Pohl et al. | |
| 7,615,662 B2 | 11/2009 | Pohl et al. | |
| 2008/0146834 A1 * | 6/2008 | Pohl et al. | 560/347 |
| 2008/0167490 A1 * | 7/2008 | Pohl et al. | 560/347 |
| 2011/0213178 A1 * | 9/2011 | Mattke et al. | 560/347 |

FOREIGN PATENT DOCUMENTS

| | | | | |
|---|---|---|---|---|
| DE | 10 2006 058 634 | | 6/2008 | |
| EP | 0749958 A1 * | | 12/1996 | ............ C07C 263/04 |
| EP | 1 319 655 | | 6/2003 | |
| EP | 1 403 248 | | 3/2004 | |
| EP | 1 555 258 | | 7/2005 | |
| EP | 1 935 875 | | 6/2008 | |
| EP | 1 935 876 | | 6/2008 | |
| WO | WO 2005/123665 A1 * | | 12/2005 | ............ C07C 263/10 |
| WO | 2007 028715 | | 3/2007 | |

OTHER PUBLICATIONS

International Search Report issued Mar. 25, 2010 in PCT/EP09/63071 filed Oct. 8, 2009.

* cited by examiner

*Primary Examiner* — Rosalynd Keys

(74) *Attorney, Agent, or Firm* — Oblon, Spivak, McClelland, Maier & Neustadt, L.L.P.

(57) ABSTRACT

The invention relates to a process for preparing isocyanates by reacting the corresponding amines with phosgene in the gas phase, if appropriate in the presence of an inert medium, in which the amine and the phosgene are first mixed and converted to the isocyanate in a reactor, and in which a reaction gas which comprises isocyanate and hydrogen chloride and leaves the reactor is cooled in a quench space of a quench by adding a quench medium. The quench medium on addition to the quench space has a temperature above the condensation temperature or the desublimation temperature of the reaction gas.

20 Claims, No Drawings

PROCESS FOR PREPARING ISOCYANATES

The invention proceeds from a process for preparing isocyanates by reacting the corresponding amines with phosgene in the gas phase, if appropriate in the presence of an inert medium, in which the amine and the phosgene are first mixed and converted to the isocyanate in a reactor, and in which a reaction gas which comprises isocyanate and hydrogen chloride and leaves the reactor is cooled in a quench space of a quench by adding a quench medium.

The preparation of isocyanates by phosgenating the corresponding amines can in principle be effected by a liquid phase or gas phase phosgenation. Gas phase phosgenation is notable in that a higher selectivity, a lower holdup of toxic phosgene and a reduced amount of energy are required.

In gas phase phosgenation, an amine-containing reactant stream and a phosgene-containing reactant stream, each in the gaseous state, are mixed. The amine and the phosgene react with release of hydrogen chloride (HCl) to give the corresponding isocyanates. The amine-containing reactant stream is generally present in the liquid phase and has to be evaporated and optionally superheated before being mixed with the phosgene-containing stream.

Corresponding processes for preparing isocyanates in the gas phase are described, for example in EP-A 1 319 655 or EP-A 1 555 258.

In order to prevent further reactions, it is necessary to cool the reaction mixture rapidly after the end of the reaction. To this end, for example, a liquid quench is used. Such a liquid quench is described, for example, in EP-A 1 403 248 or in DE-A 10 2006 058 634. The quench medium which is used for cooling has a temperature which is in the range from 50 to 200° C. The liquid stream sprayed in cools the reaction gas rapidly to temperatures generally between 100 and 200° C. This forms a biphasic mixture with an isocyanate-rich liquid phase and a low-isocyanate gas phase. The two are then sent to a common separating stage or optionally separate separating stages, for example a distillation stage for separation of hydrogen chloride and phosgene on the one hand, and isocyanate on the other hand.

A disadvantage of the known quench apparatus is, however, that the walls of the quench apparatus, especially close to the supply of the quench medium, have temperatures below the condensation or desublimation point of the reaction gas. For this reason, parts of the reaction gas may condense out or desublime as early as at these points. This condensate or desublimate has a comparatively high residence time at these points and can be subject to further reactions which have an adverse effect on the selectivity of the overall process.

In addition, the condensation or desublimation of the reaction gas can block the nozzles through which the quench medium is added. In addition, wall deposits can also form within the quench space.

It is thus an object of the present invention to provide a process for preparing isocyanates by reacting the corresponding amines with phosgene, in which condensation or desublimation of the reaction gas in the region of the addition points of the quench medium is prevented.

The object is achieved by a process for preparing isocyanates by reacting the corresponding amines with phosgene in the gas phase, if appropriate in the presence of an inert medium, in which the amine and the phosgene are first mixed and converted to the isocyanate in a reactor, and in which a reaction gas which comprises isocyanate and hydrogen chloride and leaves the reactor is cooled in a quench space of a quench by adding a quench medium. The quench medium on addition to the quench space has a temperature above the condensation temperature or the desublimation temperature of the reaction gas.

The temperature of quench medium above the condensation temperature or the desublimation temperature of the reaction gas prevents reaction gas from condensing or desubliming in the region of addition of the quench medium at the addition sites for the quench medium or on the walls of the quench space. In this way, it is possible to prevent the addition points for the quench medium from becoming blocked. The cleaning intervals for the quench apparatus can be lengthened.

To prepare the isocyanate, the phosgene and the amine are preferably first fed to a mixing zone in which amine and phosgene are mixed to give a reaction mixture. Subsequently, the reaction mixture is fed to the reactor in which the conversion to the isocyanate is effected. The conversion of amine and phosgene in the reactor is effected in the gas phase. To this end, the pressure in the reactor is preferably in the range between 0.3 and 3 bar absolute, more preferably in the range from 0.8 to 3.0 bar absolute. The temperature is preferably in the range from 250 to 500° C., especially in the range from 300 to 480° C.

In order to be able to perform the reaction in the gas phase, it is also preferred to add the amine and the phosgene in gaseous form. To this end, the amine preferably has a temperature in the range from 200 to 400° C. The pressure of the amine added is preferably in the range between 0.05 and 3 bar absolute. The temperature of the phosgene added is preferably in the range from 250 to 450° C. To this end, the phosgene is typically heated before addition in the manner known to those skilled in the art.

To heat the phosgene and the amine and to simultaneously evaporate the amine, for example, an electrical heater or direct or indirect heating by combustion of a fuel is used. The fuels used are typically fuel gases, for example natural gas. By virtue of the lowering of the boiling temperature of the amine, heating is also possible, for example by means of steam. The pressure of the steam is selected here according to the boiling temperature of the amine. A suitable vapor pressure of the steam is, for example, in the range from 40 to 100 bar. This gives rise to a temperature of the steam in the range from 250 to 311° C.

In general, it is necessary to heat the amine to the reaction temperature in a plurality of stages. In general, the amine, for this purpose, is first preheated, then evaporated and then superheated. In general, the evaporation takes the longest residence times and thus leads to decomposition of the amine. In order to minimize this, evaporation at lower temperatures, as arises, for example, through the lower pressure, is advantageous. In order to superheat the evaporated amine to reaction temperature after the evaporation, heating with steam is generally insufficient. For superheating, an electrical heater or direct or indirect heating by combustion of a fuel is therefore typically used.

In contrast to the evaporation of the amine, the phosgene is evaporated generally at significantly lower temperatures. For this reason, the phosgene can generally be evaporated using steam. However, the necessary superheating of the phosgene to heat it to reaction temperature is generally also possible only by electrical heating or direct or indirect heating by combustion of a fuel.

In order to prevent a reaction in the region of the mixing zone or to lower the reaction rate, it is advantageous to achieve turbulent flow in the mixing zone, in order to achieve rapid mixing. Moreover, it is advantageous to maintain the temperature in the mixing zone below the actual reaction temperature and to heat the reaction mixture to reaction temperature between the mixing zone and the reactor. To this end, for example, a diffuser can be used between the mixing zone and the reactor.

The reactor which is used for phosgenation of the amine to prepare isocyanates is known to those skilled in the art. In general, the reactors used are tubular reactors. In the reactor, the amine is reacted with the phosgene to give the corresponding isocyanate and hydrogen chloride. Typically, the phosgene is added in excess, such that the reaction gas which forms in the reactor, as well as the isocyanate formed and the hydrogen chloride, also comprises phosgene.

Amines which can be used to prepare isocyanates are monoamines, diamines, triamines or higher-functionality amines. Preference is given to using monoamines or diamines. According to the amine used, the corresponding monoisocyanates, diisocyanates, triisocyanates or higher-funtionality isocyanates are obtained. Preference is given to preparing monoisocyanates or diisocyanates by the process according to the invention.

Amines and isocyanates may be aliphatic, cycloaliphatic or aromatic.

Cycloaliphatic isocyanates are those which comprise at least one cycloaliphatic ring system.

Aliphatic isocyanates are those which have exclusively isocyanate groups bonded to straight or branched chains.

Aromatic isocyanates are those which have at least one isocyanate group bonded to at least one aromatic ring system.

The term "(cyclo)aliphatic isocyanates" is used hereinafter for cycloaliphatic and/or aliphatic isocyanates.

Examples of aromatic mono- and diisocyanates are preferably those having 6 to 20 carbon atoms, for example phenyl isocyanate, monomeric 2,4'- and/or 4,4'-methylenedi(phenyl isocyanate) (MDI), 2,4- and/or 2,6-tolylene diisocyanate (TDI) and 1,5- or 1,8-naphthyl diisocyanate (NDI).

Preferred (cyclo)aliphatic diisocyanates are those having 4 to 20 carbon atoms.

Examples of customary (cyclo)aliphatic diisocyanates are aliphatic diisocyanates such as 1,4-tetramethylene diisocyanate, 1,6-hexamethylene diisocyanate (1,6-diisocyanatohexane), 1,8-octamethylene diisocyanate, 1,10-decamethylene diisocyanate, 1,12-dodecamethylene diisocyanate, 1,14-tetradecamethylene diisocyanate, 1,5-diisocyanatopentane, neopentane diisocyanate, derivatives of lysine diisocyanate, tetramethylxylylene diisocyanate (TMXDI), trimethylhexane diisocyanate or tetramethylhexane diisocyanate, and 3(or 4),8(or 9)bis(isocyanatomethyl)tricyclo-[5.2.1.0$^{2\text{-}6}$]decane isomer mixtures, and cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane, 2,4- or 2,6-diisocyanato-1-methylcyclohexane.

Preference is given to 1,6-diisocyanatohexane, 1-isocyanato-3,3,5-trimethyl-5-(isocyanatomethyl)cyclohexane, 4,4'-di(isocyanatocyclohexyl)methane and tolylene diisocyanate isomer mixtures. Particular preference is given to 1,6-diisocyanatohexane, 1-isocyanato-3,3,5-trimethyl-5-(isocyanatomethyl)cyclohexane and 4,4'-di(isocyanatocyclohexyl)methane.

Amines which are used in the process according to the invention for reaction to give the corresponding isocyanates are those in which the amine, the corresponding intermediates and the corresponding isocyanates are present in gaseous form under the selected reaction conditions. Preference is given to amines which decompose over the duration of the reaction under the reaction conditions to an extent of at most 2 mol %, more preferably to an extent of at most 1 mol % and most preferably to an extent of at most 0.5 mol %. Particularly suitable amines here are especially diamines based on aliphatic or cycloaliphatic hydrocarbons having 2 to 18 carbon atoms. Examples thereof are 1,6-diaminohexane, 1,5-diaminopentane, 1,3-bis(aminomethyl)cyclohexane, 1-amino-3,3,5-trimethyl-5-aminomethylcyclohexane (IPDA) and 4,4-diaminodicyclohexylmethane. Preference is given to using 1,6-diaminohexane (HDA).

For the process according to the invention, it is likewise possible to use aromatic amines which can be converted to the gas phase without significant decomposition. Examples of preferred aromatic amines are tolylenediamine (TDA), as the 2,4 or 2,6 isomer or as a mixture thereof, for example as an 80:20 to 65:35 (mol/mol) mixture, diaminobenzene, 2,6-xylidine, naphthyldiamine (NDA) and 2,4'- or 4,4'-methylene (diphenyldiamine) (MDA) or isomer mixtures thereof. Among these preference is given to the diamines, particular preference to 2,4- and/or 2,6-TDA or 2,4'- and/or 4,4'-MDA.

To prepare monoisocyanates, it is likewise possible to use aliphatic, cycloaliphatic or aromatic amines, typically monoamines. A preferred aromatic monoamine is especially aniline.

In the gas phase phosgenation, it is desirable that the compounds which occur in the course of the reaction, i.e. reactants (amine and phosgene), intermediates (especially the mono- and dicarbamoyl chlorides which form as intermediates), end products (isocyanate), and any inert compounds metered in, remain in the gas phase under the reaction conditions. Should these or other components be deposited from the gas phase, for example on the reactor wall or other apparatus components, these deposits can undesirably alter the heat transfer or the flow through the components affected. This is especially true of occurrence of the amine hydrochlorides which form from free amino groups and hydrogen chloride, since the resulting amine hydrochlorides precipitate readily and are re-evaporable only with difficulty.

In addition to the use of a tubular reactor, it is also possible to use essentially cuboidal reaction spaces, for example plate reactors. Any desired other cross section of the reactor is also possible.

In order to prevent the formation of by-products, it is preferred to supply phosgene in excess. In order to supply only the proportion of amines needed for the reaction, it is possible to mix the amine with an inert gas. The proportion of inert gas in the amine can be used to adjust the amount of the amine supplied for a given geometry of the feed orifices for the amine and the phosgene. Inert media which can be added are those which are present in gaseous form in the reaction chamber and do not react with the compounds which occur in the course of the reaction. The inert media used may, for example, be nitrogen, noble gases such as helium or argon, aromatics such as chlorobenzene, o-dichlorobenzene, toluene, xylene, chloronaphthalene, decahydronaphthalene, carbon dioxide or carbon monoxide. Preference is given, however, to using nitrogen and/or chlorobenzene as the inert medium.

Alternatively, it is, however, also possible, for example, in order to avoid too great an excess of phosgene, to add the inert medium to the phosgene.

In general, the inert medium is added in an amount such that the ratio of the gas volumes of inert medium to amine or to phosgene is less than 0.0001 to 30, preferably less than 0.01 to 15 and more preferably less than 0.1 to 5.

In order to reduce or to prevent the formation of undesired by-products, and also to suppress decomposition of the isocyanate formed, the reaction gas is cooled in a quench space immediately after the reaction. To this end, a preferably liquid quench medium is added, which absorbs heat through evaporation and leads to rapid cooling of the reaction gas.

In order to prevent reaction products or reaction by-products from condensing in the region of the addition of the quench medium, which can thus lead, for example, to blockage of the addition points of the quench medium, the quench medium added, in accordance with the invention, has a temperature above the condensation or desublimation temperature of the reaction gas.

The quench medium is preferably added via at least one nozzle. More preferably, the quench medium is added via at least two nozzles, the nozzles preferably being positioned in homogeneous distribution in the peripheral direction at the same axial position. This can achieve homogeneous addition of the quench medium.

The temperature of the quench medium above the condensation temperature or the desublimation temperature of the reaction gas prevents the addition positions, especially the nozzles and also the walls of the quench space, from cooling to a temperature below the condensation or desublimation temperature. In this way, it is prevented that portions of the reaction gas precipitate, condense or desublime on the walls or the nozzles, which can thus lead to blockage of the nozzles or contamination of the walls.

A suitable quench medium which is added to cool the reaction gas is in principle any desired liquid which is inert toward the components present in the reaction gas. However, preference is given to using, as the quench medium, an optionally halogen-substituted hydrocarbon. The quench medium is more preferably selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, tetrahydrofuran, dimethylformamide, xylene, chloronaphthalene, decahydronaphthalene and toluene. Very particular preference is given to using monochlorobenzene as the quench medium.

In addition to the hydrocarbons optionally substituted by halogen atoms, a suitable quench medium is, however, for example, also the isocyanate.

Rapid cooling is achieved especially by adding the quench medium in finely atomized form. As a result, the quench medium has a large surface area and can rapidly absorb the heat and hence cool the reaction gas.

According to the invention, the quench medium is added in liquid form with a temperature above the condensation temperature of the reaction gas. In order to prevent premature evaporation of the quench medium, it may be necessary to increase the pressure in the feed line compared to the pressure in the quench space. The decompression to the pressure of the quench space can be achieved through the nozzles themselves or else suitable control units. The decompression of the quench medium and mixing with the hot reaction gases accomplish heating and/or partial or complete evaporation of the quench medium. The heat absorbed in the process leads to cooling of the reaction gases.

Especially in the case of use of a quench medium which has a boiling temperature below the condensation temperature of the reaction gas under the conditions in the quench space, the pressure in the feed lines is elevated compared to the pressure in the quench space in order to prevent the evaporation of the quench medium before the addition to the quench space.

The pressure with which the quench medium is added is preferably in the range from 1 to 20 bar, more preferably in the range from 1 to 10 bar and especially in the range from 1 to 8 bar.

In one embodiment of the invention, the quench may be followed by further stages for cooling the reaction gas. In the individual stages for cooling, the reaction gas is cooled further in each case, until the desired end temperature is attained, with which the reaction gas is sent, for example, to a downstream workup.

In one embodiment, at least one of the stages for cooling the reaction gas which follow the quench is a further quench.

For example, it is possible to scrub the reaction gas leaving the quench and the stages for cooling which may follow with a solvent, preferably at temperatures of more than 130° C. Suitable solvents are, for example, the same substances which can also be used as the quench medium.

In the scrubbing, the isocyanate is transferred selectively into the scrubbing solution. Subsequently, the remaining gas and the resulting scrubbing solution are preferably separated by means of rectification into isocyanate, solvent, phosgene and hydrogen chloride.

The gas mixture leaving the reactor is preferably scrubbed in a scrubbing tower, by removing the isocyanate formed from the gaseous gas mixture by condensation in an inert solvent, while excess phosgene, hydrogen chloride and if appropriate the inert medium pass through the workup apparatus in gaseous form. Preference is given to maintaining the temperature of the inert solvent above the dissolution temperature of the carbamoyl chloride corresponding to the amine in the selected scrubbing medium. The temperature of the inert solvent is more preferably maintained above the melting temperature of the carbamoyl chloride corresponding to the amine.

The scrubbing can be performed in any desired apparatus known to those skilled in the art. For example, stirred vessels or other conventional apparatus is suitable, for example columns or mixer-settler apparatus.

The reaction gas leaving the reactor is scrubbed and worked up generally as described, for example, in WO-A 2007/028715.

EXAMPLE

In a plant for preparing isocyanate, about 1.8 kg/h of TDA are phosgenated. The reaction gas stream of 15.95 kg/h which forms in the reactor has a temperature of 458° C. and comprises 15.7% by weight of TDI, 71.2% by weight of phosgene and 13.1% by weight of HCl. The dew point of the reaction gas is 183° C. The reaction gas is cooled in a quench apparatus with monochlorobenzene. To this end, the monochlorobenzene used as the quench medium is heated in liquid form to 200° C. at a pressure of 6 bar and supplied to the quench space via a spray nozzle. The pressure in the quench space is 2 bar absolute. The mixing temperature which is established in the quench space is about 157° C. About 2.15 kg/h of a TDI-rich liquid with a content of about 64% by weight of TDI, and 33.8 kg/h of a low-TDI gas phase with a TDI content of approx. 3.3% by weight, are obtained.

Owing to the feed temperature of the quench medium of 200° C. compared to the condensation temperature of the reaction gas of 183° C., the premature condensation of portions of the reaction gas and hence the formation of deposits in the region of the feed of the quench medium can be prevented.

The invention claimed is:

1. A process for preparing at least one isocyanate comprising:
    mixing at least one amine and phosgene and converting the at least one amine and the phosgene to the isocyanate in a reactor, wherein a reaction gas which comprises isocyanate and hydrogen chloride leaves the reactor and is cooled in a quench space of a quench by adding a quench medium, and wherein the quench medium on addition to the quench space has a temperature above a condensation temperature or desublimation temperature of the reaction gas.

2. The process of claim 1, wherein the at least one amine and the phosgene are reacted in the gas phase.

3. The process of claim 1, wherein the amine and the phosgene are added in gaseous form.

4. The process of claim 1, wherein the quench medium is added via at least one nozzle.

5. The process of claim 1, wherein the quench medium is an optionally halogen-substituted hydrocarbon.

6. The process of claim 1, wherein the quench medium is selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, tetrahydrofuran, dimethylformamide, xylene, chloronaphthalene, decahydronaphthalene, and toluene.

7. The process of claim 1, wherein the quench medium is added in liquid form with a temperature above the condensation temperature of the reaction gas.

8. The process of claim 1, wherein the quench medium, under conditions in the quench space, has a boiling temperature below the condensation temperature of the reaction gas, and a pressure in feed lines of the quench medium is elevated compared to a pressure in the quench space in order to prevent evaporation of the quench medium before addition to the quench space.

9. The process of claim 1, wherein the quench medium, under feed conditions, has a boiling temperature above the condensation temperature of the reaction gas.

10. The process of claim 1, wherein the quench medium is added with a pressure in a range from 1 to 20 bar.

11. The process of claim 1, wherein the quench medium is decompressed immediately after the addition, which lowers the temperature of the quench medium below the condensation temperature of the reaction gas.

12. The process of claim 1, wherein the quench medium evaporates at least partly after addition to the quench space.

13. The process of claim 1, wherein the quench is followed by at least one cooling of the reaction gas.

14. The process of claim 13, wherein at least one of the at least one cooling of the reaction gas which follows the quench, is a further quench.

15. The process of claim 1, wherein the preparing is carried out in the presence of an inert medium.

16. The process of claim 2, wherein the amine and the phosgene are added in gaseous form.

17. The process of claim 2, wherein the quench medium is added via at least one nozzle.

18. The process of claim 3, wherein the quench medium is added via at least one nozzle.

19. The process of claim 2, wherein the quench medium is an optionally halogen-substituted hydrocarbon.

20. The process of claim 3, wherein the quench medium is an optionally halogen-substituted hydrocarbon.

* * * * *